United States Patent [19]

Starling et al.

[11] 4,265,669

[45] May 5, 1981

[54] SHRINK-FREE CERAMIC AND METHOD AND RAW BATCH FOR THE MANUFACTURE THEREOF

[75] Inventors: Lynn B. Starling, Rolla, Mo.; James E. Stephan, Arvada; Robert D. Stroud, Boulder, both of Colo.

[73] Assignees: Coors Porcelain Company, Golden, Colo.; Ralph B. Sozio, Boston; Edwin J. Riley, Milton, both of Mass. ; part interest to each

[21] Appl. No.: 103,771

[22] Filed: Dec. 14, 1979

[51] Int. Cl.³ .................... C04B 35/44; C04B 35/04; C04B 35/10
[52] U.S. Cl. .................................. 106/73.4; 106/35; 264/65
[58] Field of Search ............... 106/73.4, 35; 264/65

[56] References Cited

U.S. PATENT DOCUMENTS

| 3,361,583 | 1/1968 | Elarde et al. | 106/43 |
| 3,516,810 | 6/1970 | Ivey et al. | 106/73.4 |
| 3,549,393 | 12/1970 | Elarde | 106/73.4 |
| 3,676,569 | 7/1972 | Thompson | 106/73.4 |
| 4,089,038 | 5/1978 | Bacher | 106/73.4 |

OTHER PUBLICATIONS

Ware, R. K., et al., "Porcelains Having Low-Firing Shrinkage", *Ceramic Bulletin*, vol. 43, No. 5, (1964), pp. 383–389.

*Primary Examiner*—Herbert T. Carter
*Assistant Examiner*—Mark Bell
*Attorney, Agent, or Firm*—Reising, Ethington, Barnard, Perry & Brooks

[57] ABSTRACT

The invention provides a hard, strong ceramic body and a ceramic raw batch and method for manufacture whereby the body, after being formed of the raw batch in the shape and size desired, can then be fired to monolithic structure without any shrinkage or distortion during the firing operation. The raw batch contains aluminum oxide, magnesium oxide, glass frit and a silicone resin, these constituents being present in a ratio such that after the firing operation the resulting monolithic body contains from about 70% to 95% by weight crystalline material and the remainder interstitial glass, the crystalline material consisting predominantly of magnesium aluminate spinel and alumina. The ceramic and method have particular utility for making dental crowns and other dental appliances where a precise fit along with high strength and wear resistance are desirable.

25 Claims, 1 Drawing Figure

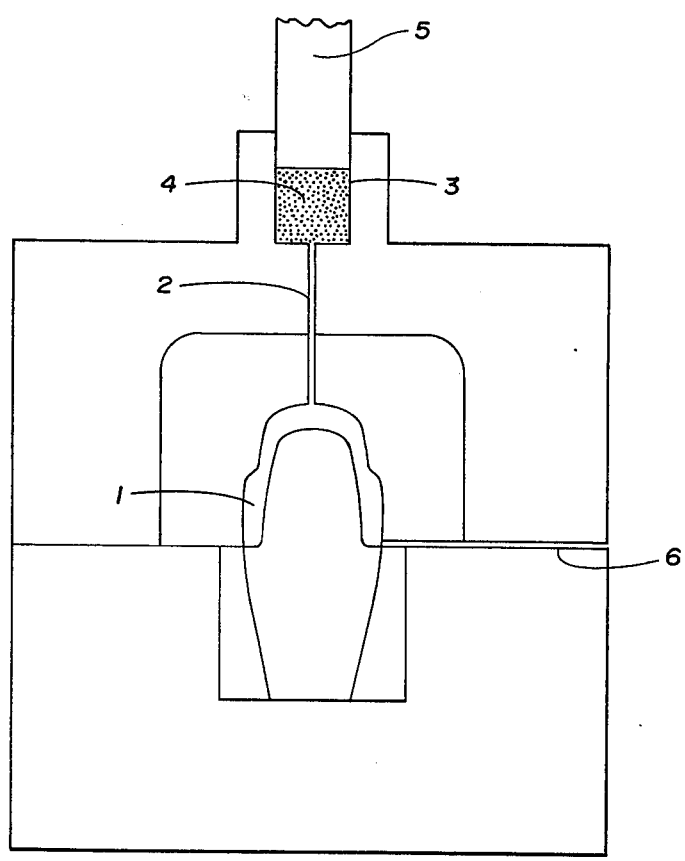

SHRINK-FREE CERAMIC AND METHOD AND RAW BATCH FOR THE MANUFACTURE THEREOF

TECHNICAL FIELD

The subject matter of the present invention is a dense, hard, fired ceramic body which can be manufactured without shrinkage during the firing operation, and a ceramic raw batch and method for making such shrink-free ceramic bodies.

BACKGROUND ART

Conventional ceramic bodies, typically alumina ceramics, are manufactured by forming a raw batch of the desired ceramic ingredients in particulate form, (e.g. aluminum oxide), plus a binder, molding or otherwise forming the raw batch into a compacted body, and then firing the compacted body to sinter or vitrify the ceramic. During the firing operation, there is considerable shrinkage—generally from about 10% to 20%—which means that the compact must be made larger than the desired fired body. Also, because shrinkage is never exactly uniform throughout the body, there is always a certain amount of warpage or distortion. With good quality control, it is possible to maintain the warpage or distortion within the bounds of normal tolerances for many kinds of ceramic bodies; however, where extremely close tolerances must be met, shrinkage and any resulting warpage or distortion are serious problems.

Shrinkage occurs for one or a combination of two reasons. First, even if high pressure is used to mold or otherwise form the compact, the density of the compact is not as high as theoretically possible—there is always considerable porosity—to the end there is some shrinkage when the compact fires to a high density non-porous monolith. The inclusion of organic binder in the batch, which is desirable to add green strength to the compact, can contribute to the porosity of the compact in that the organic binder vaporizes or burns out early in the firing operation. Secondly, where the ceramic ingredients undergo chemical or crystalline transformation during the firing, if the ceramic formed is of greater density and lesser volume than the raw ceramic ingredients, then this also contributes to the shrinkage.

Various shrink-free ceramics have been proposed, as discussed in the article entitled "Porcelains Having Low-Firing Shrinkage", page 383, volume 43, No. 5 (1964) *Ceramic Bulletin* of the American Ceramic Society. U.S. Pat. No. 3,549,393 Elarde also discloses such ceramics. In the latter, the ceramic raw batch formulations include kyanite which converts to mullite and silica during firing with a resultant volume increase to compensate for the shrinkage which would otherwise occur. But the problem with such ceramics has been that they are relatively low in physical strength and wear resistance and hence are subject to deterioration when used in applications where high strength and wear resistance are important for optimum performance. One such application is that of dental crowns or the like dental appliances, and in this regard reference is here made to U.S. patent application Ser. No. 103,647 filed concurrently herewith, on Dec. 14, 1979, in the names of Ralph B. Sozio and Edwin J. Riley and entitled DENTAL APPLIANCE AND METHOD OF MANUFACTURE. Briefly that patent application is directed to a dental crown, or other dental appliance, and method wherein a cardinal feature is that the appliance is formed of shrink-free ceramic whereby a substantially perfect fit can be attained between the dental appliance and the prepared tooth to which the appliance is to be secured. The invention of this instant patent application provides an improved shrink-free ceramic which is not only shrink free but which is also possessed of increased strength and wear resistance, and hence of particular utility for the practice of the invention covered by said patent application in the names of Ralph B. Sozio and Edwin J. Riley.

DISCLOSURE OF THE INVENTION

The ceramic raw batch of the present invention contains as its essential ingredients at least 50% by weight aluminum oxide, at least 5% by weight magnesium oxide, from about 5% to 25% by weight glass frit, and from about 10% to 15% by weight silicone resin preferably having an SiO content of at least 50% by weight of the silicone, the aluminum oxide content of the raw batch being at least twice that stoichiometrically required to react with all the magnesium oxide in the batch to form magnesium aluminate spinel. Since alumina and magnesia react mole for mole to form the spinel, this means that the number of moles of alumina should be at least twice the number of moles of magnesia.

The raw batch is formed, as by molding, into a self-sustaining compact of the shape and size desired, the silicone resin functioning, in the compact, as a binder which provides good green strength. The compact is then fired to a dense, hard monolithic body, during which firing there is no shrinkage to the end that the fired body is of a shape and size substantially identical to the shape and size of the compact prior to firing. The ratio of ingredients in the raw batch and the firing temperature and schedule used in the firing operation are such that during firing the magnesium oxide, or at least most of it, reacts with some of the aluminum oxide to form magnesium aluminate spinel ($MgAl_2O_4$) while the frit along with silica from the silicone resin react to form a glass phase. Because magnesium aluminate spinel occupies a greater volume than does the combination of the magnesium oxide and aluminum oxide reacting to form the spinel, there is a resultant volume increase sufficient to compensate for the volume decrease which would otherwise occur during the maturing of the relatively porous compact to the substantially non-porous fired monolithic body. The fired body contains crystalline material in an amount from about 70% to 95% by weight of the body, and the remainder an interstitial glass, the crystalline material being at least about 70% by weight aluminum oxide and magnesium aluminate spinel and the remainder, if any, a crystalline aluminum silicate. In the preferred embodiments the glass is an alkaline earth alumino silicate glass and the crystalline material includes crystalline alkaline earth alumino silicate. Because of the high alumina and spinel content of the crystalline material and because of the glass phase which occupies substantially all space between crystals of the crystalline material, the fired body is not only substantially non-porous but is characterized by high hardness, and hence wear resistance and by high flexural and compressive strength. The fired bodies made in accordance with the preferred embodiments of the invention have a density of at least about 2.7 g/cc. which is upwards of 80% of theoretical (i.e. the theoretically highest density possible for the ceramic composition used), meaning that the bodies are substantially non-porous; a hardness in excess of 35 on the Rockwell 45N scale; a flexural strength in excess of 15,000 psi; a compressive strength in excess of 60,000 psi; and a low coefficient of thermal expansion, below $8 \times 10^{-6}$/C.

In the preferred embodiments of the invention the glass frit is an alkaline earth alumino silicate glass; however it can, if desired, be another glass or a fritted oxide or combination of oxides which react with silica to form glass. Also in the preferred embodiment a small amount of kaolin, about 3% to 5% by weight, is included in the raw batch to provide improved flow characteristics in the forming of the compact.

To best accomplish the desired shrink-free characteristic along with the desired high strength and wear resistant properties, the most preferred ratio of ingredients in the raw batch is: for each 7 parts by weight aluminum oxide, about 1 part by weight magnesium oxide, from about 1 to 2 parts by weight glass frit and about 1.5 parts by weight of the silicone resin.

For attainment of high compaction density in the prefired compact, it is preferable that the particulate ceramic ingredients of the raw batch be of variated particle size, ranging from submicron to 200 mesh Tyler, and that the raw batch additionally include a small amount of one or more organic compounds which function as lubricants, allowing the particles to slide with respect to each other, during the molding or other compaction operation.

The desired reaction between the magnesium oxide and aluminum oxide to form spinel, along with the reaction to form the glass phase, is best obtained by firing to a temperature of about 1300° C., and with the firing at least up to about 650° C. being in an oxidizing atmosphere and preferably on a gradual firing schedule, all as will be discussed in detail hereinafter.

Particularly for the practice of the invention for making dental appliances, it is preferred that the raw batch be pressed or otherwise formed into small discs for use in molding the dental crowns or other appliances by transfer molding, as will also be discussed in greater detail hereinafter.

BEST MODE FOR CARRYING OUT THE INVENTION

Raw Batch Formulation and Processing

The aluminum oxide used should preferably be alpha alumina and should preferably be of variated particle size. A mixture of approximately one third tabular alumina of −325 mesh Tyler and two thirds Alcoa A-15 alumina of a particle size of 0.4 to 10 microns (average, 2.5 microns) is excellent. The magnesium oxide used can typically be of −200 mesh Tyler.

As has already been stated, the silicone resin used should preferably have an SiO content of at least 50% by weight. The silicone resin currently marketed by General Electric Company designated as SR350 and containing upwards of 60% SiO is excellent for the practice of the invention.

As the glass frit we prefer to use an alkaline earth alumino silicate frit. However, other glasses, or fritted oxides or combinations of oxides which react with silica to form glass, can be used. Examples are the alkali alkaline earth silicate glasses (or the oxides which react with silica to form same) and borosilicate glasses (or the borates which react with silica to form same). Where, as is preferred, an alkaline earth alumino silicate glass is used, barium is the preferred alkaline earth metal for such silicate. A 200 Tyler mesh size for the frit is satisfactory.

If, as is preferred, some kaolin is included in the batch, it is, of course, best that it be one of high plasticity and purity. Edgar Plastic Kaolin is excellent.

The organic lubricant included in the raw batch can be any of those well known in the ceramics art—for example stearic acid and the metal stearates, waxes and oils. The organic lubricant, like the organic portion of the silicone resin, vaporizes or burns out during the firing operation.

For the processing of the raw batch it is preferred that the batch ingredients, except for the silicone resin, first be dry milled, as in a ball mill, to form a uniform mixture thereof, which mixture is then blunged in a solution of the silicone resin in an organic vehicle thereby to form a homogeneous slurry. Then the solvent is removed by evaporation at low temperature, and the dry batch either simultaneously or thereafter reduced to small particle size. As a preferred technique the slurry is spray dried at low temperature, e.g. room temperature (to prevent cross linking of the silicone resin), thereby to form a dry flowable particulate mixture which is excellent for further processing of the raw batch to form the compacts.

The following is a preferred formulation and processing procedure for the raw batch:

| Ingredient | Weight | Weight % |
|---|---|---|
| Al$_2$O$_3$ (particle size, 0.4 to 10 microns Avg. 2.5 microns) | 100 grams | 43.29 |
| Al$_2$O$_3$ (−325 mesh, Tyler) | 40 grams | 17.32 |
| MgO (−200 mesh, Tyler) | 20 grams | 8.66 |
| BaO . SiO$_2$ . Al$_2$O$_3$ glass (53% BaO, 42% SiO$_2$, 5% Al$_2$O$_3$) | 30 grams | 12.99 |
| Silicone Resin (General Electric SR350 upwards of 60% by weight SiO) | 28 grams | 12.12 |
| Edgar Plastic Kaolin | 9 grams | 3.90 |
| Calcium Stearate | 2 grams | .86 |
| Acrawax C (steryl amide wax, melting temperature 290° F.) | 2 grams | .86 |

It will be noted that in this preferred formulation the ratio of key ingredients on a weight basis is: 7 parts aluminum oxide, 1 part magnesium oxide, about 1.5 parts barium aluminum silicate glass frit and about 1.5 parts silicone resin.

All of the other ingredients other than the silicone resin are placed in a ball mill and are dry milled therein for about 5 minutes to attain a uniform mixture. The silicone resin is dissolved in about 70 ml of a suitable organic solvent, such as Chlorothene Nu (1,1,1 trichloroethane), and the dry mixture from the ball milling operation is then mixed, as by blunging, into the solution of the silicone resin until a homogeneous slurry is obtained. The slurry is then spray dried at about room temperature, thereby resulting in the desired dry flowable powder mixture.

Forming the Compact

Any of various techniques well known in the ceramics art can be used to form the batch into a self-sustaining compact of the shape and size desired. In this regard it should be noted that the silicone resin is first heat softenable and then thermosetting. For example, the silicone resin used in the above formulation softens at about 30° C. and hardens at about 150° C. Hence techniques requiring a thermoplastic binder or techniques requiring a thermosetting binder can be used. For purposes of molding the overall batch formulation can be considered as a highly filled organic polymer, and since the silicone resin softens prior to curing to its thermoset stage, it can be either compression molded at a temperature to cause it to cure or it can be injection molded at a lower temperature at which it remains a thermoplastic and then later cured. Further, even at low temperature the silicone resin has sufficient binding properties to enable the raw batch to be dry pressed in matched dies into self-sustaining bodies at room temperature. Amongst the other techniques which can be used is isostatic molding which is also well known in the art and which involves the use of an elastomeric mold to which hydraulic or the like external pressure is applied thereby to compress and compact the ceramic raw batch contained therein into a self-sustaining compact. However, the preferred manner of forming the compact for the manufacture of dental crowns or other dental appliances is that of transfer molding. For transfer molding the raw batch is first formed into a pre-form, preferably a disc-shape pre-form, as by dry pressing in matched metal dies at a temperature not in excess of the softening temperature of the silicone resin, and this pre-form is then subsequently transfer molded to form the dental crown, or other dental appliance, to the precise shape desired. For the transfer molding the pre-form is heated to the softening temperature of the silicone resin whereby the pre-form is rendered flowable, whereupon pressure is applied to force the flowable mixture of the pre-form into the mold, the pressure being maintained, and the mold being heated sufficiently to thermoset the silicone resin binder.

Reference is now made to the drawing which diagrammatically shows a transfer molding apparatus for forming the raw batch into a compact for the manufacture of a tooth crown. In the drawing the mold cavity for forming the tooth crown-shaped compact is shown at 1, there being an inlet port 2 extending from the mold cavity to a chamber 3 which receives the disc-shaped pre-formd 4 of the raw batch, a plunger 5 being provided to apply pressure to the pre-form after it is heat-softened thereby to force the flowable raw batch through the port into the mold cavity. For the transfer molding of the preferred raw batch set forth above it is preferred that the mold cavity, inlet port and chamber be preheated to about 150° C. whereupon the pre-form is inserted into the chamber with the plunger thereover and, after the pre-form has become softened, which only requires about 1 minute because of the small size of the pre-form, approximately 1,500 psi pressure is applied by way of the plunger thereby forcing the heat-softened material of the pre-form into the mold cavity. Air escapes from the mold cavity through a vent 6. The 1,500 psi pressure is maintained for about 5 minutes during which the mold cavity temperature remains at about 150° C. At the end of the 5 minutes the resin is sufficiently cured and the mold can be disassembled and the shaped compact removed for firing.

Irrespective of the manner in which the compact is formed, it is preferred that it have a density as high as practically attainable. With the preferred embodiments of the invention the density of the preferred compact is approximately the same as that of the fired body, at least 2.7 g/cc. Where transfer molding is used the pre-form should, of course, have a total volume which at least slightly exceeds the aggregate volume of the mold cavity and the inlet port.

Firing Operation

To sinter the ceramic to a dense monolithic body with substantially zero shrinkage, the compact is heated to a temperature sufficient to cause the reaction of the magnesium oxide with a portion of the aluminum oxide to form magnesium aluminate spinel and to cause the formation of the interstitial glass. It is preferred that the firing be to a temperature of approximately 1300° C. and it is preferred that the firing to this temperature be on a gradual schedule, with rise in temperature from room temperature to about 650° C. not exceeding about 200° C. per hour, and with one or more soaks for an aggregate of at least about six hours soak time, at one or more temperatures, within the range of from about 400° C. to 700° C. The following is a specific preferred firing schedule for the raw batch formulation set forth above: From room temperature to 500° C., about 160° C./hour; hold at 500° C. for sixteen hours; from 500° C. to 650° C. about 150° C./hour; hold at 650° C. for eight hours; from 650° C. to 1315° C., about 420° C./hour; firing complete and hence ceased when 1315° C. is reached. It will be understood, of course, that the best firing temperature to which the ceramic is fired, will depend on the precise batch formulation, 1315° C. plus or minus 10° C. being the best firing temperature for the specific batch formulation listed above.

At least during the early stages of firing, re up to about 650° C., the firing should be in an oxidizing atmosphere in order to convert the SiO to $SiO_2$; firing all the way through the firing schedule in the ambient atmosphere is quite satisfactory. During the firing up to about 650° C. there is burn out or vaporization of the organics of the organic lubricants, and there is burn out or vaporization of the organic portion of the silicone resin. The purpose of the gradual firing schedule and hold time is in connection with the burn out or vaporization of the organic portion of the silicone resin. That is, if there is rapid heating a substantial portion of the SiO groups of the silicone resin can accompany the vaporization or burn out of the organic portion of the silicone resin. In terms of attaining the desired shrink-free characteristic while yet attaining a fired body which is substantially non-porous, the loss of SiO groups during firing works against the purpose served by the silicone resin having the high SiO content—which purpose is to provide excellent binding properties and moldability prior to firing while yet contributing little, if anything, to the effective porosity of the compact prior to firing. By means of the gradual firing schedule and the hold time, escape of SiO groups is minimized to the end that substantially all of the SiO content of the silicone resin converts to $SiO_2$ which remains in the fired body.

Since the silicone resin used in the aforesaid preferred embodiment contains something in excess of 60% by weight SiO groups and since, during the subsequent firing operation in an oxidizing atmosphere, the SiO converts to $SiO_2$, the 28 grams of silicone resin contribute something in excess of 23 grams of $SiO_2$ to the ceramic mix. This $SiO_2$, which is very reactive ends up in the fixed body as alkaline earth alumino silicate, either crystalline or as glass.

During the portion of the firing schedule subsequent to about 700° C., the magnesium oxide reacts with aluminum oxide, commencing at about 900° C., and at the same time, or thereafter, the highly reactive $SiO_2$ derived from the silicone resin reacts with the glass frit, and also with the kaolin and with some of the aluminum oxide and some of the magnesium oxide, to generate siliceous glass which forms as a continuous interstitial phase. Thereafter, probably during cooling subsequent to firing, a portion of the glass phase crystallizes out as a crystalline aluminum silicate—in the preferred embodiment as an alkaline earth alumino silicate, all or most of which has been identified, in the preferred embodiment, as being an alkaline earth osumulite, $BaMg_2Al_3(Si_9Al_3O_{30})$.

Composition and Properties of the Fired Monolithic Body

Where the aforesaid most preferred raw batch formulation and the aforesaid most preferred firing schedule therefor are used, analysis and petrographic examination of the resultant fired monolithic body show it to contain crystalline material in an amount in excess of 90% by weight of the body, and the remainder an interstitial glass phase of alkaline earth alumino silicate glass, and with the crystalline material being about 40% by weight alpha alumina, about 40% by weight magnesium aluminate spinel, and about 20% by weight barium osumulite. Such preferred body has a density of about 2.80 g/cc., a porosity of only about 0.2%, flexural strength of about 17,200 psi, a compressive strength of about 72,000 psi, a hardness of about 41 on the Rockwell 45N scale and a coefficient of thermal expansion of about $6.3 \times 10^{-6}/°C$. and with a size and shape substantially identical to the size and shape of the pre-fired body.

Commensurate with attaining the desired shrink-free characteristic, the higher the aggregate percentage of alumina and magnesium aluminate spinel in the crystalline material the better. However, if the amount of magnesium aluminate spinel generated during firing is too great, the expansion resulting therefrom can exceed that required to compensate for the shrinkage which would otherwise occur with the result that the fired body will be larger than the pre-fired body. It is to the end of attaining a fired body which has the desired excellent strength and hardness characteristics and which is substantially identical in size to the pre-fired body that, in the preferred embodiments, the raw batch formulation and the firing are such that in the fired body the percentage by weight of the magnesium aluminate spinel and the percentage by weight of the aluminum oxide in the crystalline material are approximately equal and, more importantly, with the aggregate of the two being at least about 70% by weight of the total of the crystalline material. It will be understood, however, that the formulation can be such as to generate a larger amount or a lesser amount of the spinel during firing, and this is desirable if the pre-fired body has a porosity of a magnitude which requires the generation of an increased or decreased amount of the spinel in order to compensate for the amount of shrinkage which would otherwise occur. The high strength and hardness characteristics of the fired bodies stem from the fact that the bodies contain a high percentage of crystalline material and from the fact that a high percentage of the crystalline material consists of aluminum oxide and magnesium aluminate spinel; however, the strength and hardness do not appear to depend on the exact ratio between the aluminum oxide and the magnesium aluminate spinel and hence the precise ratio can be selected with a view to attaining the desired shrink-free characteristic rather than with a view to further improving the strength and hardness characteristics.

It will be understood that while the invention has been described particularly with reference to the preferred embodiments thereof, various changes and modifications may be made all within the full and intended scope of the claims which follow.

What is claimed is:

1. A fired substantially nonporous and shrink-free ceramic body containing crystalline material in an amount of from about 70% to 95% by weight of the body and the remainder interstitial glass, said crystalline material containing aluminum oxide and magnesium aluminate spinel in an aggregate amount of at least about 70% by weight of the crystalline material, said magnesium aluminate spinel being formed in situ during the firing of said ceramic body thereby to cause expansion which compensates for shrinkage which would otherwise occur.

2. A ceramic body as set forth in claim 1 having a density of at least 2.7 g/cc., a flexural strength of at least 15,000 psi, a compressive strength of at least 60,000 psi and a hardness of at least 35 on the Rockwell 45N scale.

3. A ceramic body as set forth in claim 1 wherein said glass is an alkaline earth alumino silicate glass.

4. A ceramic body as set forth in claim 1 wherein said glass is barium alumino silicate glass.

5. A ceramic body as set forth in claim 1 wherein said crystalline material additionally includes a crystalline aluminum silicate.

6. A ceramic body as set forth in claim 5 wherein said aluminum silicate is an alkaline earth osumulite.

7. A ceramic body as set forth in claim 5 wherein said aluminum silicate is barium osumulite.

8. A ceramic body as set forth in claim 1 wherein the aluminum oxide and magnesium aluminate spinel are present in said crystalline material approximately in equal amounts.

9. A ceramic body as set forth in claim 1 wherein the crystalline material is present in an amount of at least about 90% by weight of said body and includes a crystalline alkaline earth alumino silicate, and wherein said glass is an alkaline earth alumino silicate glass.

10. A ceramic body as set forth in claim 9 wherein said crystalline alkaline earth alumino silicate is barium osumulite and wherein said glass is a barium aluminum silicate.

11. A shrink-free ceramic raw batch for forming into a shaped raw body and then firing to a fired body substantially the same in size and shape as the raw body, said batch consisting essentially of at least 50% by weight particulate aluminum oxide, at least 5% by weight particulate magnesium oxide, from about 5% to 25% by weight glass frit and from about 10% to 15% by weight silicone resin, the amount of aluminum oxide being at least twice that stoichiometrically required to react with all of the magnesium oxide to form magnesium aluminate spinel in situ during firing.

12. A ceramic raw batch as set forth in claim 11 wherein said silicone resin contains at least 50% by weight SiO.

13. A ceramic raw batch as set forth in claim 12 wherein said glass frit is an alkaline earth alumino silicate glass.

14. A ceramic raw batch as set forth in claim 12 wherein said glass frit is a barium aluminum silicate glass.

15. A ceramic raw batch as set forth in claim 12 which additionally includes from about 3% to 5% by weight kaolin.

16. A ceramic raw batch as set forth in claim 12 wherein the particle size range of the aggregate of said aluminum oxide, magnesium oxide and glass frit is from sub-micron to about 200 mesh Tyler.

17. A ceramic raw batch as set forth in claim 12 containing about seven parts by weight aluminum oxide, about one part by weight magnesium oxide, from about one to two parts by weight glass frit and about 1.5 parts by weight silicone resin containing at least 60% by weight SiO.

18. A ceramic raw batch as set forth in claim 12 wherein said aluminum oxide is alpha aluminum oxide.

19. A method for making a ceramic body comprising the steps of:
preparing a raw batch consisting essentially of at least 50% by weight particulate aluminum oxide, at least 5% by weight particulate magnesium oxide, from about 5% to 25% by weight glass frit and from about 10% to 15% by weight silicone resin containing at least 50% by weight SiO, the amount of aluminum oxide being at least twice that stoichiometrically required to react with all of the magnesium oxide to form magnesium aluminate spinel;
forming the raw batch into a self-sustaining compact having a shape and size substantially identical to the shape and size of the body desired to be made and
firing said compact in an oxidizing atmosphere at a temperature sufficient to decompose the silicone resin and to cause the SiO of the silicone resin to convert to $SiO_2$ and then further firing the compact at a temperature sufficient to cause at least most of the magnesium oxide to react with some of the aluminum oxide to form magnesium aluminate spinel, and to cause formation of an interstitial glass phase, the formation of said magnesium aluminate spinel during said firing causing expansion which compensates for shrinkage which would otherwise occur.

20. A method as set forth in claim 19 wherein said raw batch is prepared by first forming a dry uniform mixture of said aluminum oxide, said magnesium oxide and said glass frit, mixing said dry mixture with a solution of said silicone resin thereby to form a slurry, and then removing the solvent from said slurry.

21. A method as set forth in claim 20 wherein said solvent is removed by spray drying said slurry.

22. A method as set forth in claim 19 wherein said raw batch is formed into said self-sustaining compact by first forming said raw batch into a pressed pre-form and then transfer molding said pre-form.

23. A method as set forth in claim 19 wherein said compact is fired to a temperature of about 1300° C.

24. A method as set forth in claim 23 wherein said firing is in the oxidizing atmosphere at least up to about 700° C. and is on a schedule wherein the rise in temperature from room temperature to about 650° C. does not exceed about 170° C. per hour and wherein there are one or more soaks for an aggregate of at least about six hours of soak time at one or more temperatures within the range of from about 400° C. to 700° C.

25. A pressed self-sustaining raw substantially shrink-free ceramic body for use as a pre-form for transfer molding and for subsequent firing to a fired body, said raw body consisting essentially of a uniform mixture containing at least 50% by weight aluminum oxide, at least 5% by weight magnesium oxide, from about 5% to 25% by weight glass frit and from about 10% to 15% by weight silicone resin containing at least 50% by weight SiO, the amount of aluminum oxide being at least twice that stoichiometrically required to react with all of the magnesium oxide to form magnesium aluminate spinel during said firing, said aluminum oxide, magnesium oxide and glass frit being in particulate form and bonded together by said silicone resin, the particle size range of the aggregate of the aluminum oxide, magnesium oxide and glass frit being from submicron to about 200 mesh Tyler.

* * * * *